United States Patent
Ortiz et al.

(10) Patent No.: US 10,221,208 B2
(45) Date of Patent: Mar. 5, 2019

(54) METHODS OF PRODUCING AN HIV MATURATION INHIBITOR

(71) Applicant: ViiV HEALTHCARE UK (NO.4) LIMITED, Brentford, Middlesex (GB)

(72) Inventors: Adrian Ortiz, New Brunswick, NJ (US); Maxime Soumeillant, New Brunswick, NJ (US); Scott A. Savage, New Brunswick, NJ (US); Neil A. Strotman, New Brunswick, NJ (US); Martin D. Eastgate, New Brunswick, NJ (US); Matthew W. Haley, New Brunswick, NJ (US); Jeanne Ho, New Brunswick, NJ (US); Jeffrey A. Nye, New Brunswick, NJ (US); Zhongmin Xu, New Brunswick, NJ (US); Susanne Kiau, New Brunswick, NJ (US); Tamas Benkovics, East Brunswick, NJ (US); Yichen Tan, New Brunswick, NJ (US)

(73) Assignee: VIIV HEALTHCARE UK (NO.4) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/563,635

(22) PCT Filed: Apr. 14, 2016

(86) PCT No.: PCT/US2016/027504
§ 371 (c)(1),
(2) Date: Oct. 2, 2017

(87) PCT Pub. No.: WO2016/168447
PCT Pub. Date: Oct. 20, 2016

(65) Prior Publication Data
US 2018/0072691 A1    Mar. 15, 2018

Related U.S. Application Data

(60) Provisional application No. 62/147,237, filed on Apr. 14, 2015.

(51) Int. Cl.
| | |
|---|---|
| C07D 295/155 | (2006.01) |
| C07J 63/00 | (2006.01) |
| A61P 31/18 | (2006.01) |
| A61K 31/58 | (2006.01) |
| A61K 45/06 | (2006.01) |

(52) U.S. Cl.
CPC ............. C07J 63/008 (2013.01); A61K 31/58 (2013.01); A61K 45/06 (2013.01); A61P 31/18 (2018.01); C07D 295/155 (2013.01)

(58) Field of Classification Search
CPC ............................ C07J 63/008; C07D 295/55
USPC ......................................................... 544/58
See application file for complete search history.

(56) References Cited

FOREIGN PATENT DOCUMENTS

| | | |
|---|---|---|
| WO | WO 2012/106190 A1 | 8/2012 |
| WO | WO 2013/169578 A1 | 11/2013 |
| WO | WO 2014/014647 A1 | 1/2014 |

*Primary Examiner* — Kahsay Habte
(74) *Attorney, Agent, or Firm* — Robert H. Brink; Kathryn A. Lutomski; Edward R. Gimmi

(57) ABSTRACT

A method for producing HIV maturation inhibitor compound is set forth using betulin

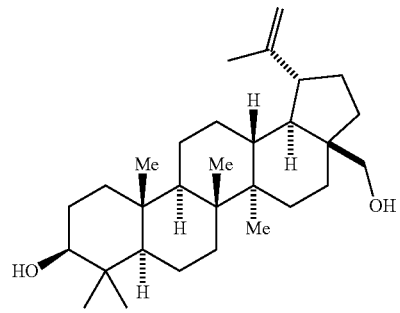

as starting material, and utilizing Lossen rearrangement techniques.

15 Claims, No Drawings

METHODS OF PRODUCING AN HIV MATURATION INHIBITOR

This application is a § 371 of International Application No. PCT/US2016/027504, filed 14 Apr. 2016, which claims the benefit of U.S. Provisional Application No. 62/147,237, filed 14 Apr. 2015.

FIELD OF THE INVENTION

The present invention generally relates to methods for producing an HIV maturation inhibitor compound and intermediates useful in the manufacture of the compound as well as pharmaceutical compositions and methods of treating HIV using the compound.

BACKGROUND OF THE INVENTION

HIV-1 (human immunodeficiency virus-1) infection and AIDS (acquired immune deficiency syndrome) remains a major medical problem. According to UNAIDS, at the end of 2014 nearly 37 million people were living with HIV. The number of cases of HIV has risen rapidly. In 2005, approximately 5.0 million new infections were reported, and 3.1 million people died from AIDS. Therefore, novel anti-HIV agents exhibiting distinct resistance patterns, and favorable pharmacokinetic as well as safety profiles are needed to provide more treatment options.

An emerging class of compounds for the treatment of HIV are called HIV maturation inhibitors. Maturation is the last of as many as ten or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

The HIV maturation triterpenoid compound of Formula 1, below:

Formula I

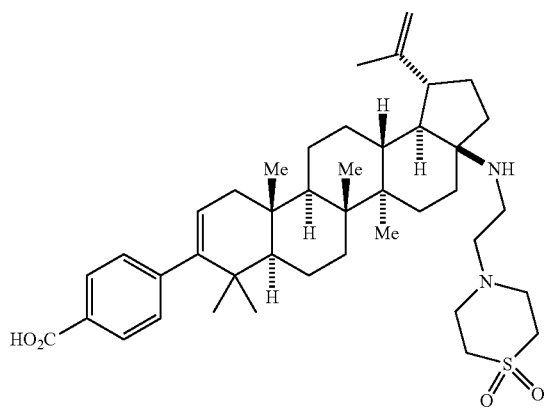

has been set forth and described in PCT Patent Application Publication No. WO 2012/106190 A1, published Aug. 9, 2012, and its US equivalents US Patent Application No. US 2013/0035318 A1, published Feb. 7, 2013 and U.S. Pat. No. 8,846,647 B2, issued Sep. 30, 2014, which are incorporated herein by reference. These documents describe and set forth various methods for making the compound of Formula I. This compound is also known by the IUPAC name 4-((1R,3aS,5aR,5bR,7aR,11aS,11bR,13aR,13bR)-3a-((2-(1,1-dioxidothio morpholino) ethyl)amino)-5a,5b,8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl) benzoic acid.

Although the methods known in the art for producing the compound of Formula I may be useful, new processes are desired that can enhance the efficiency of producing the compound.

SUMMARY OF THE INVENTION

In accordance with the present invention, methods of producing the compound of Formula I are provided. In accordance with the present invention, it is now possible to produce the compound of Formula I in a viable and efficient manner using betulin as a starting material. In addition, methods of producing intermediates useful in the production of the compound of Formula I are also provided. Furthermore, pharmaceutical compositions comprising the compound of Formula I and methods for treatment of disease by administering the compounds of Formula I are provided.

DETAILED DESCRIPTION OF THE INVENTION

The singular forms "a", "an", and "the" include plural reference unless the context dictates otherwise.

Where appropriate, when a substituent is not specified, it is understood that it is hydrogen.

Those terms not specifically set forth herein are intended to have the meaning which is commonly understood and accepted in the art. In some instances herein, chemical reagents and/or moieties have been identified by their commonly accepted letter abbreviations known in the art.

The invention is intended to include all pharmaceutically acceptable salt forms of the compounds disclosed herein, e.g., the compound of Formula I. Pharmaceutically acceptable salts are those in which the counter ions do not contribute significantly to the physiological activity or toxicity of the compounds and as such function as pharmacological equivalents.

The invention is intended to include all polymorphic forms of the compounds disclosed herein, e.g., the compound of Formula I. The terms "polymorph(s)" or "polymorphic form(s)", as used herein, refer to crystalline forms having the same chemical composition but different spatial arrangements of the molecules, atoms, and/or ions forming the crystal.

The invention is intended to include all isotopes of atoms occurring in the compounds disclosed herein, e.g., the compound of Formula I. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The term "pharmaceutically acceptable," as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The term "therapeutically effective amount," as used herein, is intended to include an amount of the compound of Formula I that is effective when administered alone or in combination to treat HIV.

The term "treating" as used herein, refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "alkyl" as used herein, refers to a straight or branched saturated hydrocarbon comprised of 1 to 10 carbons, and preferably 1 to 6 carbons.

The term "aryl" as used herein, refers to a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic group include, but are not limited to, phenyl, biphenyl, cyclopropylphenyl, indane, naphthalene, and tetrahydronaphthalene. The aryl group can be attached to the parent structure through any substitutable carbon atom in the group and the aryl group can be substituted with substituents known to those skilled in the art.

In one aspect of the invention, there is provided a method for making a compound of Formula I:

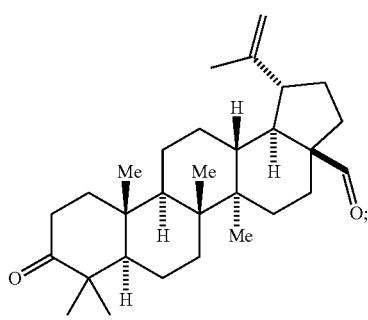

I which comprises:
(a) oxidizing betulin to form a compound of Formula I

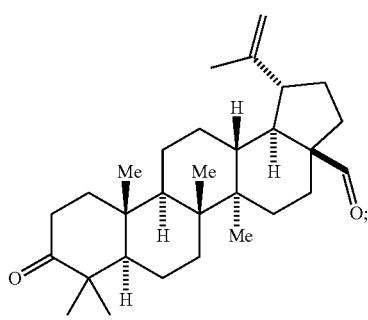

1

(b) contacting compound 1 with a compound of Formula 2a

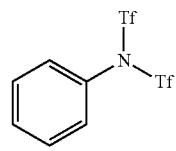

2a in the presence of a reagent to form a compound of Formula 2b

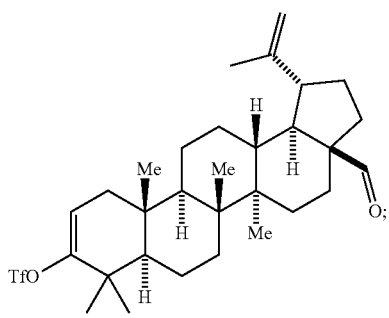

2b (c) contacting compound 2b with a compound of Formula 3a

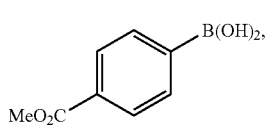

3a in the presence of PdCl$_2$Xantphos and aqueous K$_3$PO$_4$ to form a compound of Formula 3b

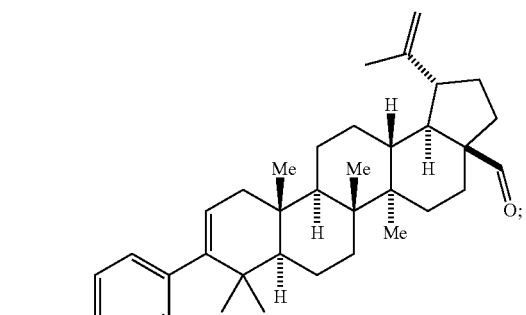

3b (d) contacting compound 3b with hydroxylamine to form a compound of Formula 4

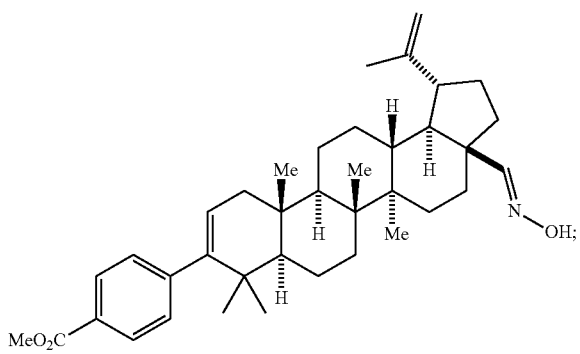

(e) contacting compound 4 with an oxidant to form a compound of Formula 5

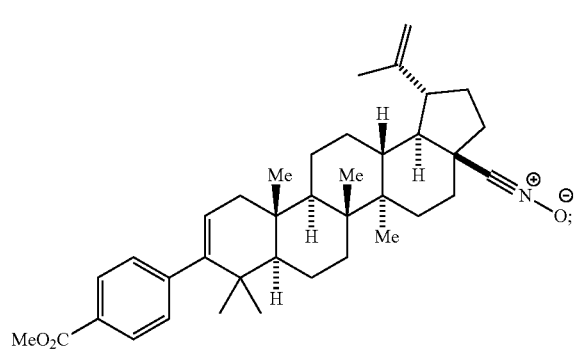

(f) contacting compound 5 with TFAA and water to form a compound of Formula 6b

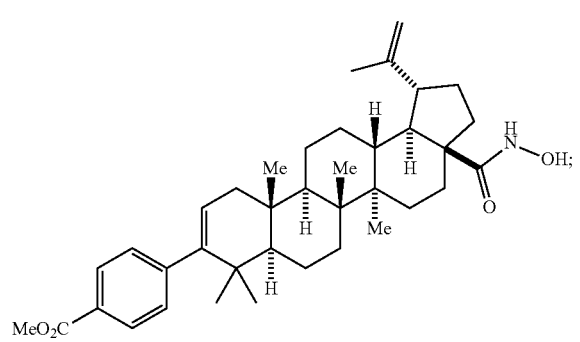

(g) contacting compound 6b with a base and heat to form a compound of Formula 7

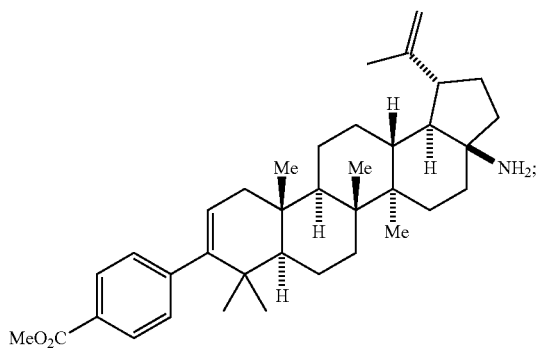

(h) contacting compound 7 with a compound of Formula 8

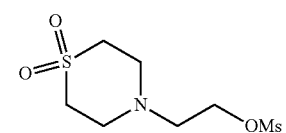

and i-Pr₂NEt and CH₂Cl₂ to form a compound of Formula 9

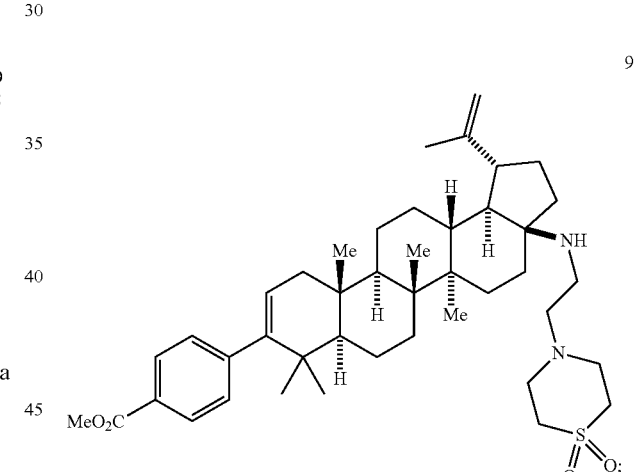

and
(i) contacting compound 9 with an aqueous base to form the compound of Formula I.

In an aspect of the invention, the oxidation in step (a) is performed in the presence of a solvent comprising a carbodiimide and dimethylsulfoxide (DMSO) in dichloromethane. In an aspect of the invention the carbodiimide is selected from 1-ethyl-3-(3-dimethylaminopropyl)carbodiimide (EDC), diisopropylcarbodiimide (DIC) and dicyclohexylcarbodiimide (DCC). In an aspect of the invention the carbodiimide is ethyl-3-(3-dimethylaminopropyl)carbodiimide.

An aspect of the invention further comprises utilizing a catalytic acid in step (a). In an aspect of the invention, the catalytic acid is selected from para-toluene sulfonic acid (p-TSA), pyridinium p-toluenesulfonate (PPTS), dichloroacetic acid, and H₃PO₄. In an aspect of the invention, the catalytic acid is pyridinium p-toluenesulfonate.

In an aspect of the invention, the reagent in step (b) is selected from lithium diisopropyl amide (LDA) and M-HMDS (hexamethyldisilazane), wherein M is selected from Na, K, or Li. In an aspect of the invention, the reagent is sodium hexamethyldisilazide (NaHMDS).

In an aspect of the invention, step (c) is conducted in the presence of a solvent. In an aspect of the invention, the solvent is tetrahydrofuran (THF).

In an aspect of the invention, the oxidant in step (e) is phenyliodine (bis)trifluoroacetate (PIFA).

In an aspect of the invention, the base in step (g) is 1,8-Diazabicyclo[5.4.0]undec-7-ene (DBU).

In an aspect of the invention, the base in step (i) is n-Bu$_4$NOH in isopropyl alcohol (IPA) or THF.

In an aspect of the invention, the oxidation in step (a) is performed using a modified Parikh-Doering oxidation that uses SO$_3$ triethylamine and DMSO in dichloromethane or THF as solvents in the presence of triethylamine (TEA) base. In an aspect of the invention, the oxidation in step (a) is performed using a modified Parikh-Doering oxidation that uses an activator selected from the group of SO$_3$·pyridine, SO$_3$-Me$_3$N and P2O$_5$. In an aspect of the invention, the base is selected from the group of diisopropylethylamine (DIPEA) and N,N-dicyclohexyl methylamine. In an aspect of the invention, the oxidation in step (a) is performed using an aerobic oxidation employing a copper (I)/dimethoxybipyridine/8-hydroxy-8-azabicyclo[3.2.1]octan-3-one/TEMPO/NMI catalyst system under O$_2$ or air in CH$_3$CN and DCM.

In an aspect of the invention, the activator is SO3-Me$_3$N and base is 1,8-Diazabicyclo[5.4.0]undec-7-ene (DBU) or 2-tert-butyl 1,1,3,3-tetramethyl guanidine (t-Bu TMG).

In an aspect of the invention, the base in step (i) is diisopropylethylamine (DIPEA)

In an aspect of the invention, there is provided a method for making a compound of Formula I:

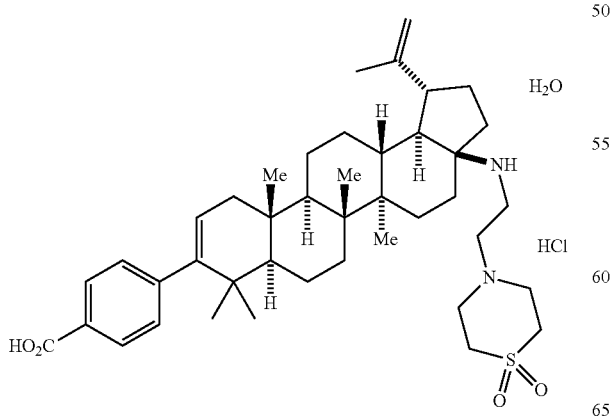

which comprises:

(a) oxidizing betulin to form a compound of Formula 1

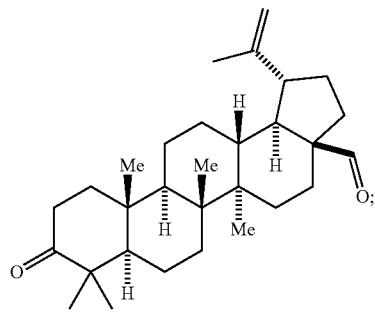

(b) contacting compound 1 with a compound of Formula 2a

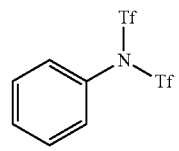

in the presence of a reagent to form a compound of Formula 2b

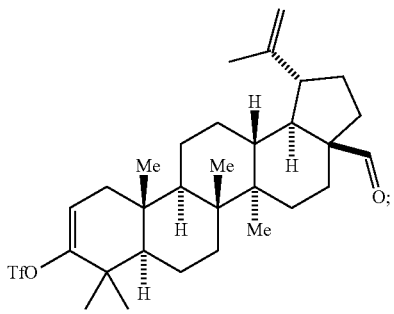

(c) contacting compound 2b with a compound of Formula 3a'

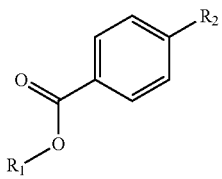

wherein R$^1$ is selected from alkyl, aryl, and substituted aryl, and R$_2$ is selected from a boronic acid, pinacolboronate ester, or isopropyl boronate ester, said contacting being conducted in the presence of PdCl$_2$xantphos and aqueous K$_3$PO$_4$ to form a compound of Formula 3b'

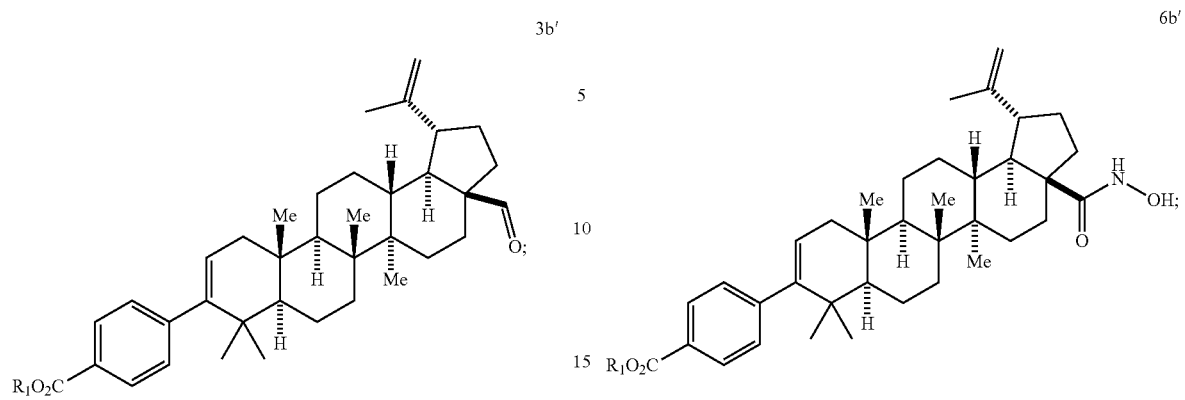

(d) contacting compound 3b' with hydroxylamine to form a compound of Formula 4'

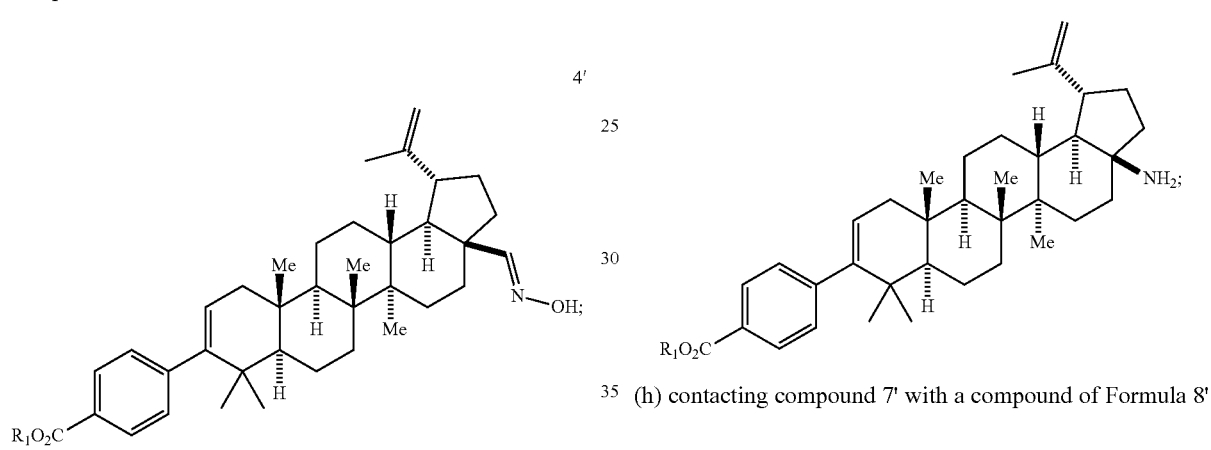

(e) contacting compound 4' with an oxidant to form a compound of Formula 5'

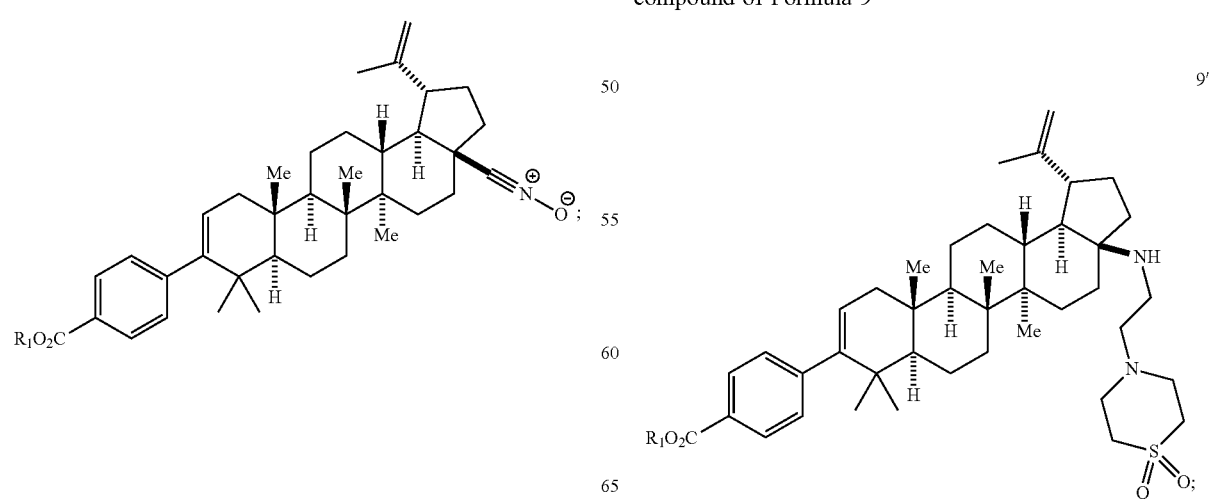

(f) contacting compound 5' with TFAA and water to form a compound of Formula 6b'

(g) contacting compound 6b with a base and heat to form a compound of Formula 7'

(h) contacting compound 7' with a compound of Formula 8' wherein X is selected from mesylate, besylate, triflate, nonaflate, tosylate, chloride, bromide and iodide, to form a compound of Formula 9' and (i) contacting compound 9' with an aqueous base to form the compound of Formula I.

In an aspect of the invention, there is provided a method for making a compound of Formula 7':

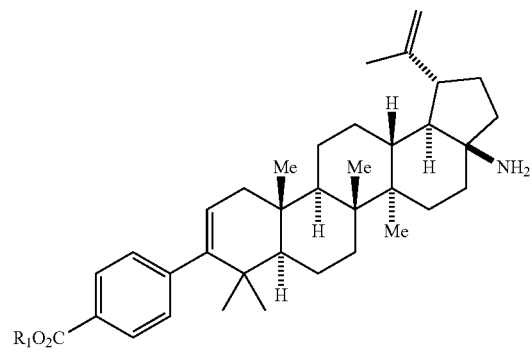

wherein $R^1$ is selected from alkyl, aryl, and substituted aryl, which comprises:

(a) contacting a compound 4' with an oxidant to form a compound 5'

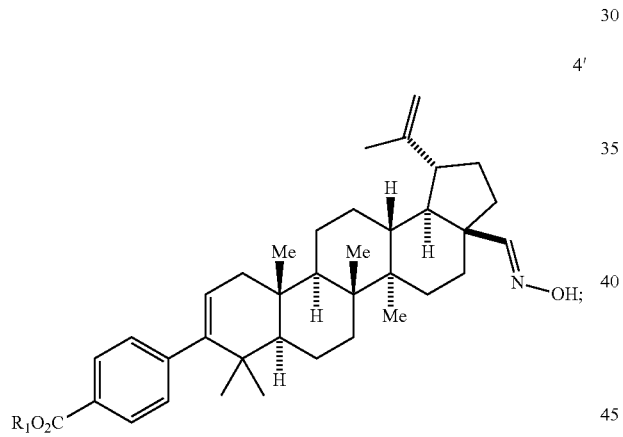

(b) contacting compound 5' with TFAA and water to form a compound 6b'

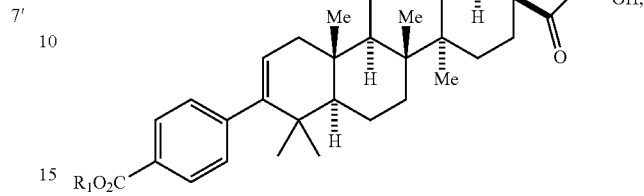

and (c) contacting compound 6b' with a base and heat to form the compound of Formula 7.

Described another way, one aspect of the invention is directed to a process for making the compound of Formula I:

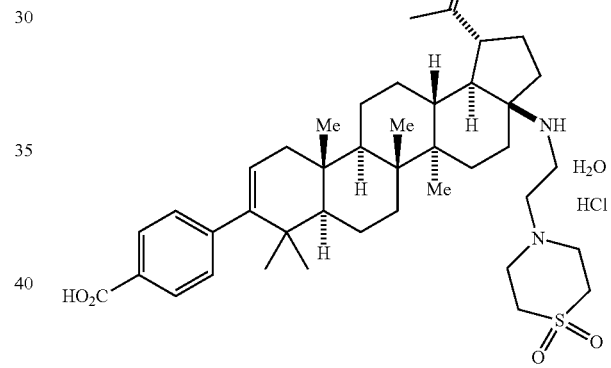

which comprises:

(1) oxidizing the starting compound

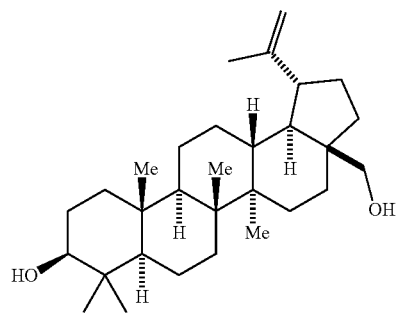

Betulin to yield compound 1;

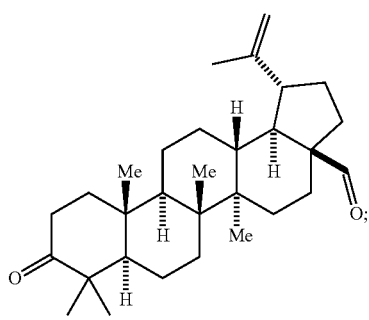

(2) contacting the compound 1 with reagent 2a

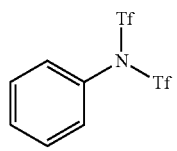

in solution to yield the compound 2b;

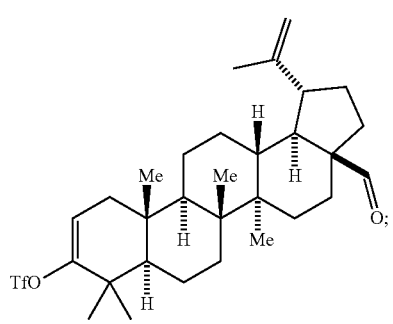

(3a) contacting the compound 2b with compound 3a,

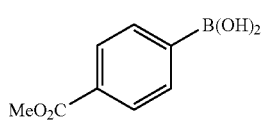

along with PdCl$_2$Xantphos and aqueous K$_3$PO$_4$ in solvent to yield 3b,

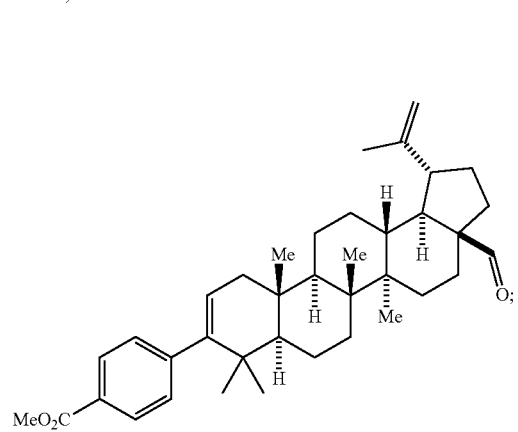

(3b) contacting the compound 3b with hydroxylamine to produce the compound 4

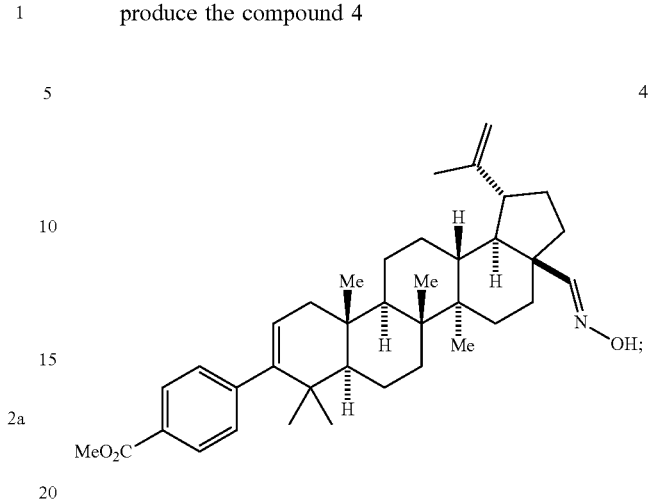

(4a) contacting the compound 4 with an oxidant to produce the compound 5

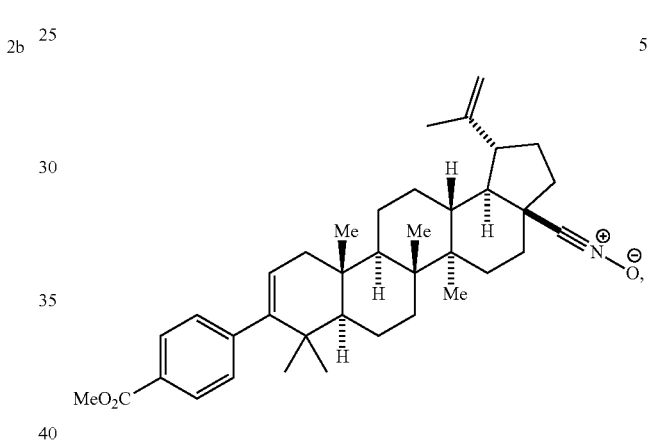

(4b) reacting compound 5 with TFAA and water to produce compound 6b,

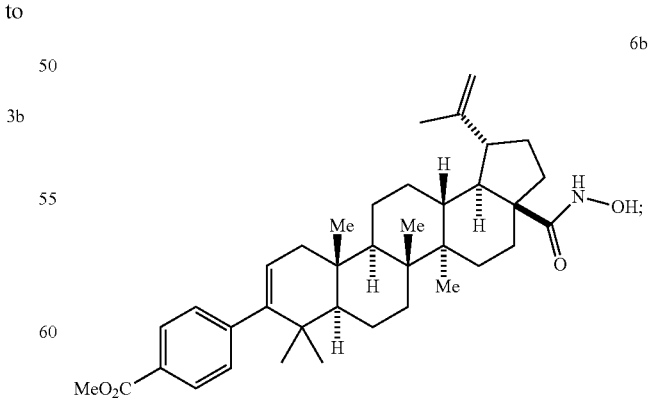

(4c) contacting the compound 6 with a base and heat to produce the compound 7 as a result of a skeletal rearrangement;

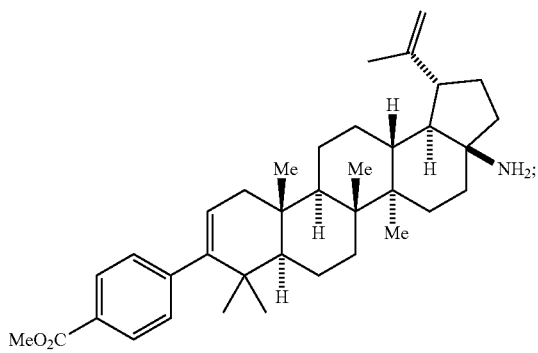

7

(5) contacting the compound 7 with compound 8

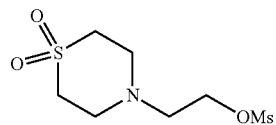

8 and base in solvent to yield compound 9

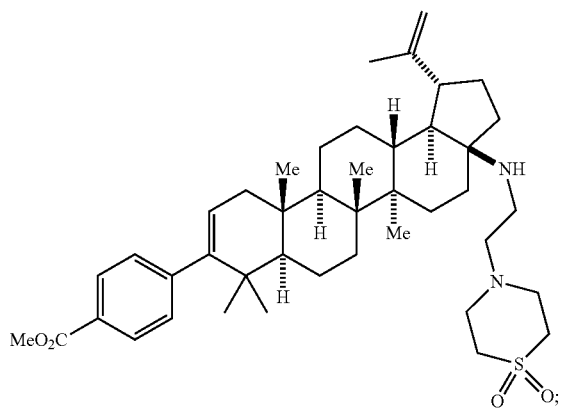

9 and (6) contacting compound 9 with an aqueous base to effect hydrolysis of the methyl ester to yield the compound of Formula I.

In an aspect of the invention, there are provided intermediate compounds which are selected from

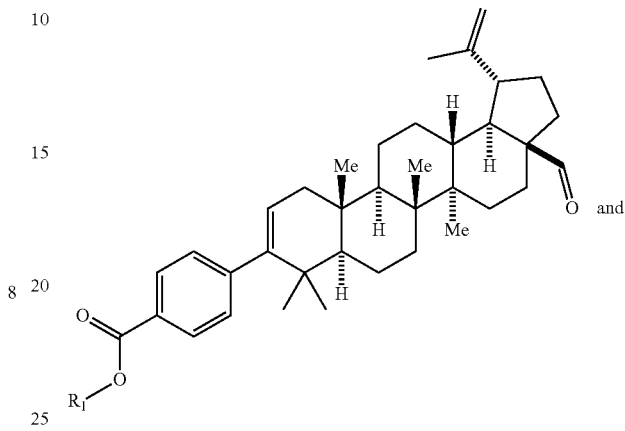

and

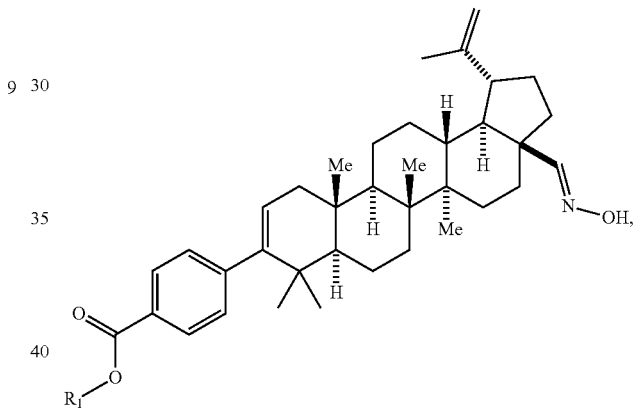

wherein $R_1$ is selected from methyl, ethyl, iso-propyl, tert-butyl and phenyl.

The invention may also be illustrated according to the following non-limiting chemical flow diagram:

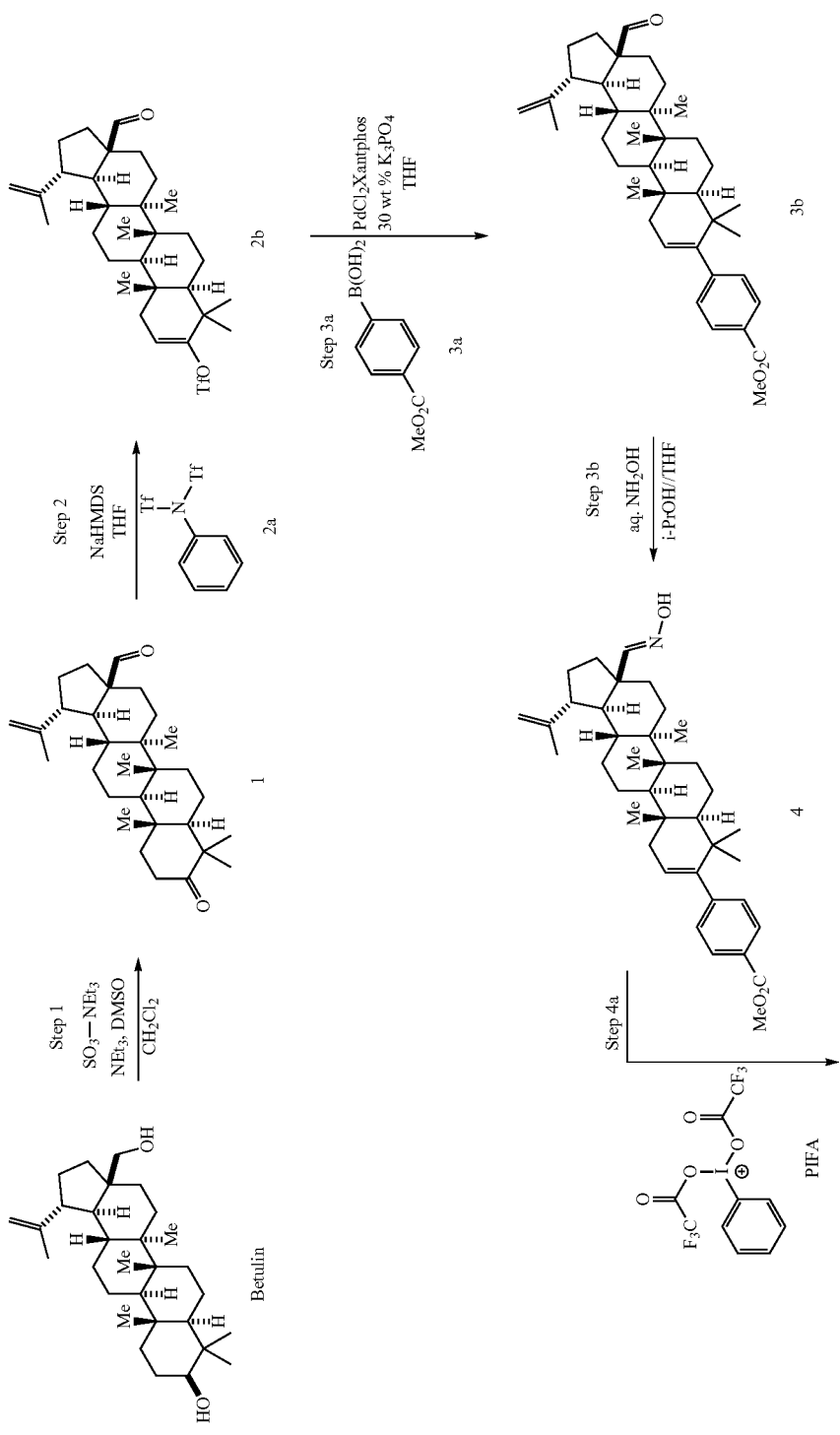

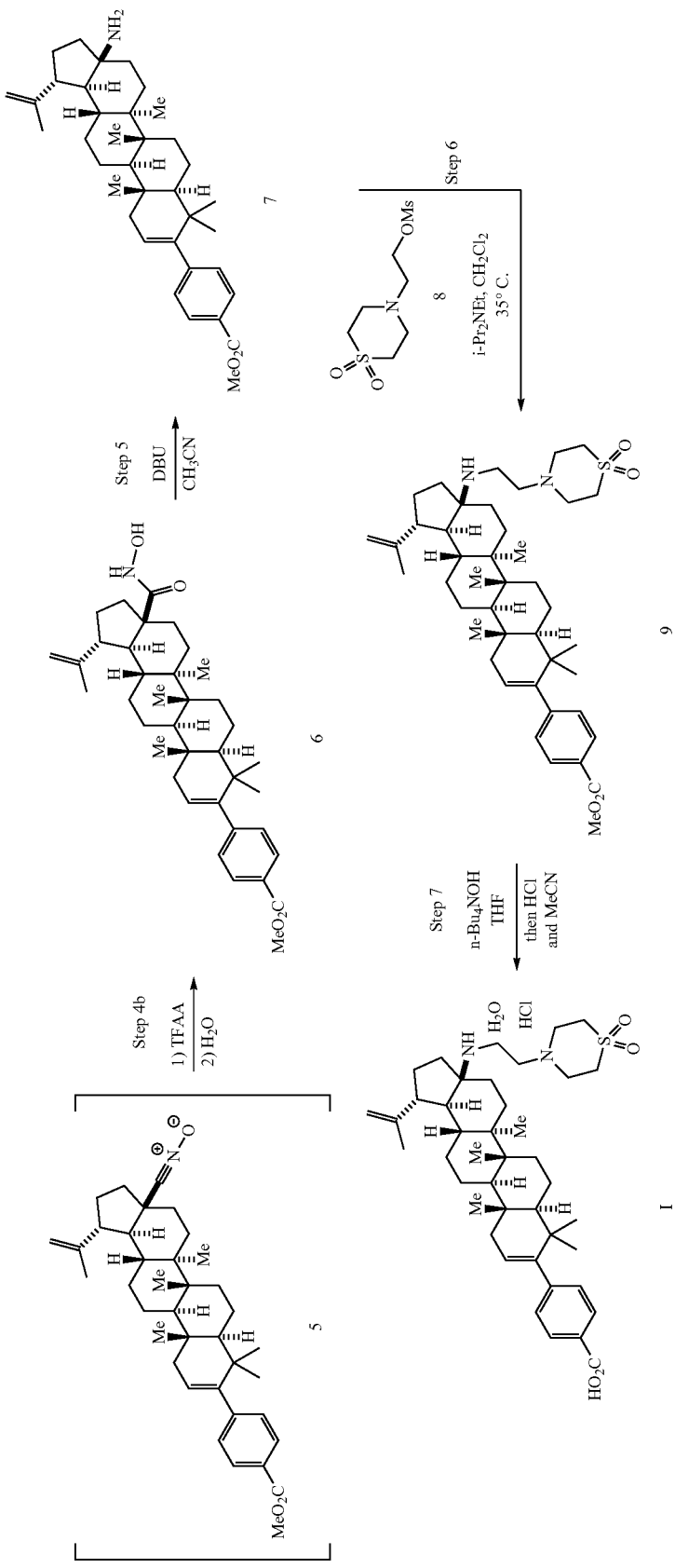

In a further aspect, the invention is also directed to one or more of each of the individual sub-steps 1, 2, 3a-b, 4a-b, 5, 6, and 7 above, whether alone or in tandem.

In another aspect of the invention, there is also provided each of the intermediate compounds 1, 2b, 3b, 4, 5, 6, 7 and 9.

A further aspect of the invention is directed to the compound of Formula I which is produced according to the process(es) herein set forth.

EXAMPLES

The following examples are provided by way of illustration only, and should not be construed as limiting the scope of the invention.

Step 1: Preparation of Compound 1

This process involves the oxidation of both hydroxyl groups present in the starting material (betulin) to produce the desired keto-aldehyde 1. Three oxidative processes have been developed to achieve the desired initial transformation: [1] A Moffatt Oxidation employing 1-Ethyl-3-(3-dimethylaminopropyl)carbodiimide (EDC) and dimethyl sulfoxide (DMSO) in dichloromethane as solvent and a catalytic acid. Various cabodiimides can be employed, including, for example, diisopropylcarbodiimide (DIC) and dicyclohexylcarbodiimide (DCC). The identity of the activating catalytic acid can also vary, and include p-toluene sulfonic acid (p-TSA), Pyridinium p-toluenesulfonate (PPTS), dichloroacetic acid, or $H_3PO_4$. Of these, PPTS is preferred. [2] An aerobic oxidation employing a copper (I)/dimethoxybipyridine/8-hydroxy-8-azabicyclo[3.2.1]octan-3-one/TEMPO/NMI catalyst system under $O_2$ or air in $CH_3CN$ and DCM. Other ligands such as bipyridine or N-benzylimidazole can also be employed. Other possible catalysts include ABNO, keto-ABNO, AZADO, and AZADOL but 8-hydroxy-8-azabicyclo[3.2.1]octan-3-one is preferred. It should be noted, that the use of 8-hydroxy-8-azabicyclo[3.2.1]octan-3-one as the oxidation catalyst precursor is preferred over the nitrosyl radical precursors such as ABNO, keto-ABNO AZADO, or AZADOL for commercial manufacturing because of its ease of preparation (2 steps) and its improved stability profile. [3] A modified Parikh-Doering oxidation that uses $SO_3$.triethylamine ($SO_3$-$Et_3N$) and DMSO in dichloromethane or THF as solvents in presence of triethylamine (TEA) base. Although $SO_3$.triethylamine is preferred in this transformation, various other activators can be employed such as $SO_3$-$Me_3N$, $SO_3$.pyridine, and $P2O_5$. In addition, other bases such as 2-tert-butyl 1,1,3,3-tetramethyl guanidine (t-Bu TMG, Barton's base), diisopropylethylamine (DIPEA) and N,N-dicyclohexyl methylamine can also be utilized, although trimethylamine (TEA) is preferred.

The reaction scheme may be summarized as follows:

Scheme 1:

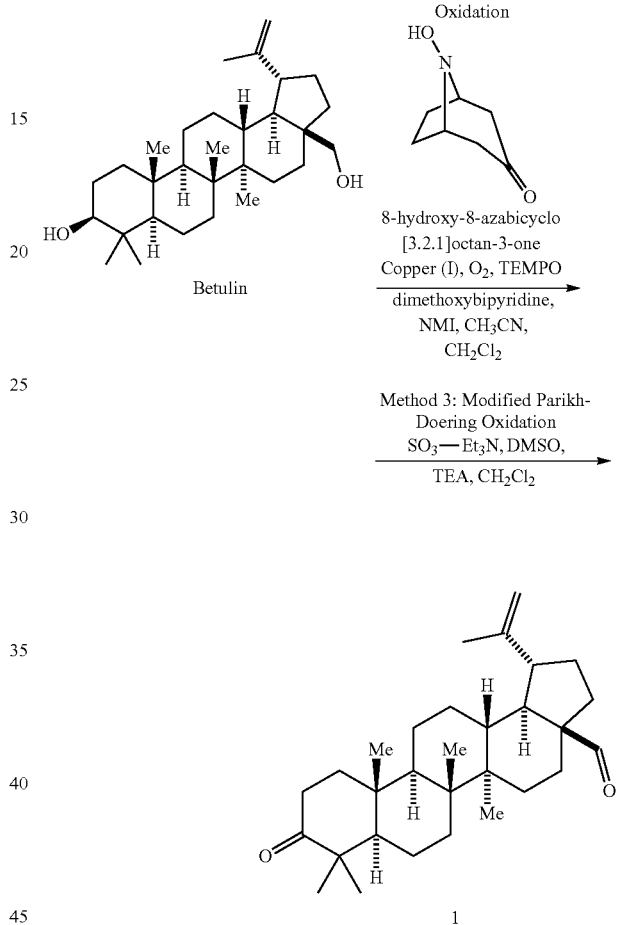

Step 2: Preparation of Compound 2

The subsequent transformation comprises the conversion of keto-aldehyde compound 1 to enol-triflate compound 2. In the optimized process, 1 and 2a are dissolved into a solvent (typically, tetrahydrofuran (THF) or methyl tert-butyl ether (MTBE)), cooled to about −5° C. The ketone in this mixture is then selectively enolized by the addition of a strong base. It is preferred to perform this reaction using the bases lithium diisopropyl amide (LDA) or M-HMDS (hexamethyldisilazane), where M=Na, K, or Li. Without being bound by any particular theory, there are two particular aspects of this reaction: (1) preference for one carbonyl group over the other (i.e. reaction with the ketone in the presence of the aldehyde), which eliminates the potential protecting group requirement, and (2) the utilization of the reagent 2a which enables a selective and non-cryogenic reaction to be conducted. Other triflating reagents such as triflic anhydride are preferably not utilized as they will react with the base used for enolization.

Scheme 2:

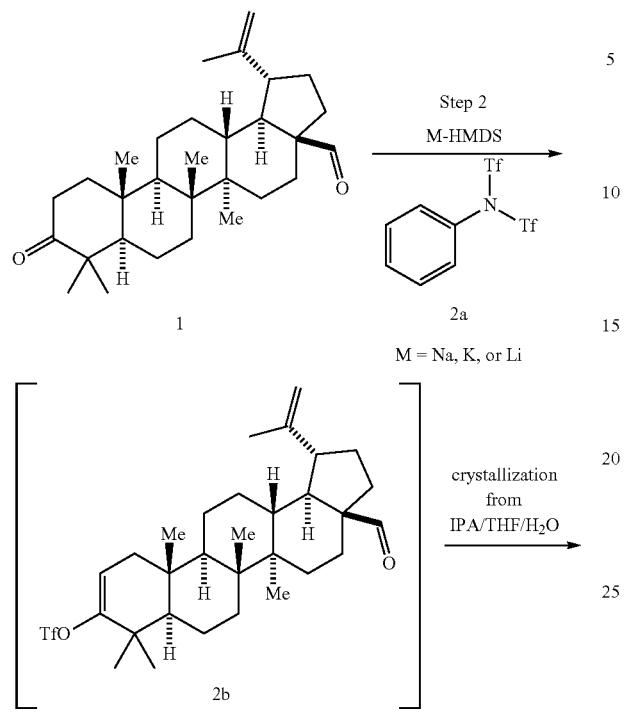

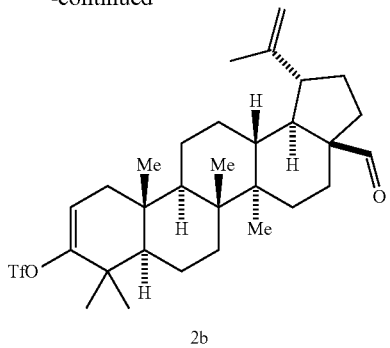

Step 3: Preparation of Compound 3

In this sub-step, boronic acid 3a is coupled to enol-triflate compound 2b via a palladium catalyzed Suzuki coupling reaction. The product intermediate shown below is telescoped through a sub step in which hydroxyl amine is condensed with the aldehyde moiety to give oxime 4 after crystallization from aqueous isopropyl alcohol (IPA). The preferred pH for this transformation is 7.0-7.5 and is obtained by a pH adjustment using a mild organic acid, such as acetic acid. This palladium mediated cross coupling occurs under the influence of the Xantphos ligand, aq. $K_3PO_4$ as base, and THF as solvent. Many bidentate and monodentate phosphine ligands for the palladium catalyst are competent, but $PdCl_2$Xantphos is preferred.

The reaction scheme for step 3 may be summarized as follows:

Scheme 3:

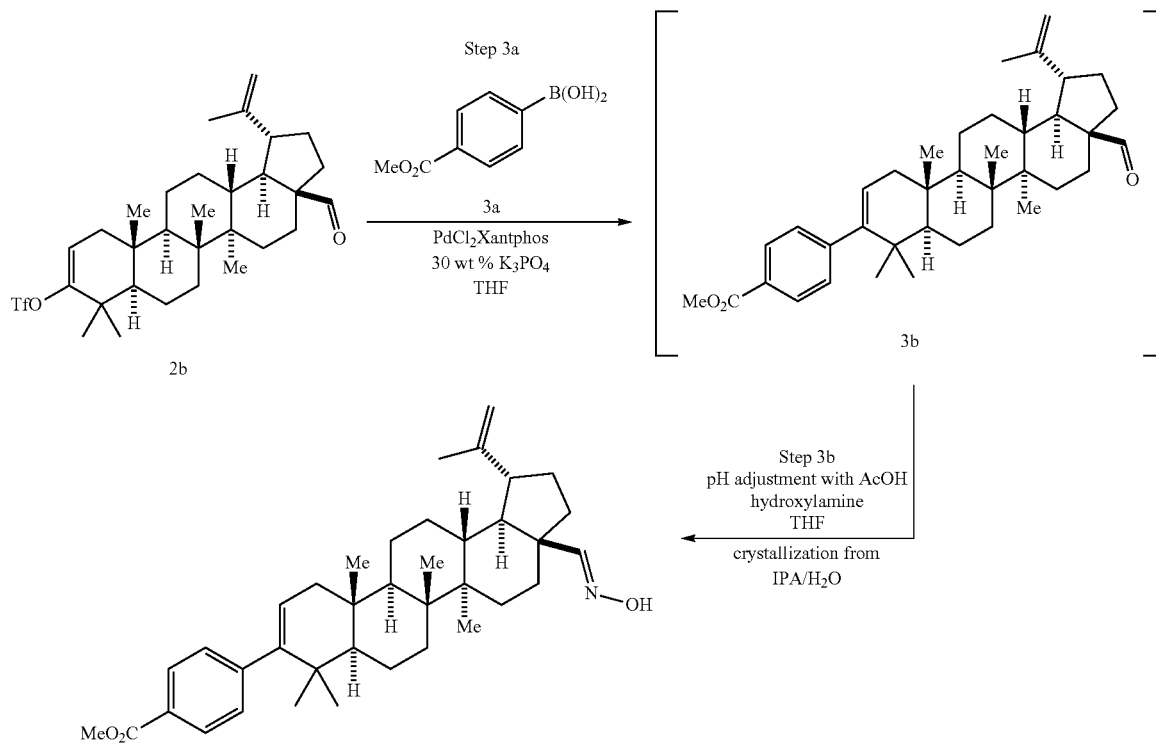

In a further aspect of the invention, compounds 3b and 4 may be represented as:

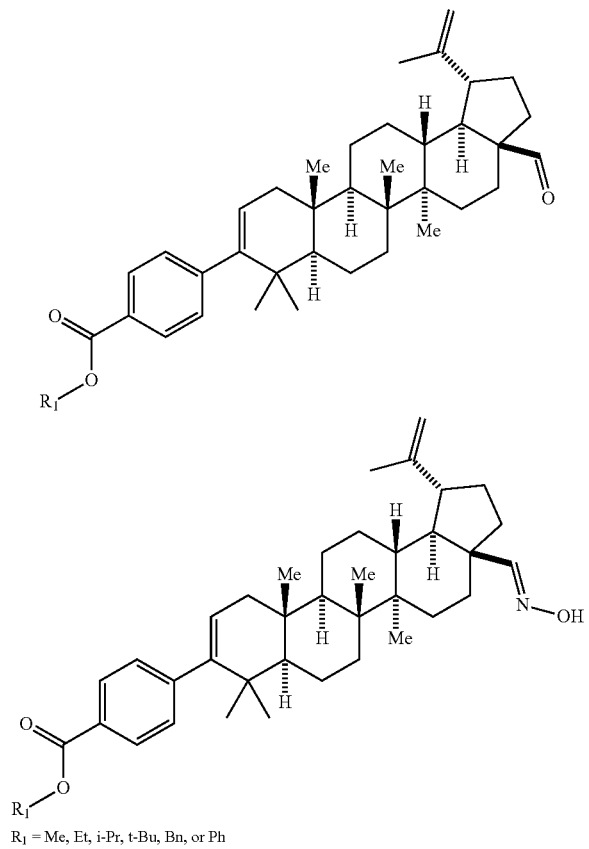

R₁ = Me, Et, i-Pr, t-Bu, Bn, or Ph wherein R¹ is selected from the group of -alkyl, -aryl, and substituted aryl, with methyl being preferred.

In a further aspect of the invention, compound 3a may be represented as:

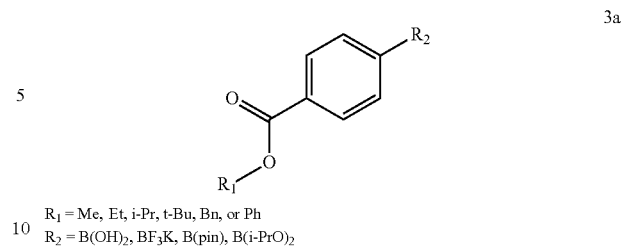

R₁ = Me, Et, i-Pr, t-Bu, Bn, or Ph
R₂ = B(OH)₂, BF₃K, B(pin), B(i-PrO)₂ wherein R¹ is selected from the group of -alkyl, -aryl, and substituted aryl, with methyl being preferred, and also wherein R₂ is either a boronic acid, pinacolboronate ester, or isopropyl boronate ester.

Step 4: Preparation of Compound 6

This is a three sub-step process involving: [1] the selective oxidation of the oxime (4) with a hypervalent iodine (III) reagent to generate the nitrile oxide (5), [2] selective hydration of the nitrile oxide using trifluoroacetic anhydride (TFAA, 0° C.) to produce bis-TFA-derivative 6a, [3] hydrolytic removal of the two TFA groups to give hydroxamic acid 6b. This selective sequence enables site specific oxidation (PIFA) and hydration (TFAA) of the oxime moiety to produce hydroxamic acid 6b in excellent yields (typically about 85-95% yield).

In this first sub step (Step 4a), [Bis(Trifluoroacetoxy)iodo]benzene (PIFA) is used preferably as the stoichiometric oxidant (about 1.0-1.25 eq) and is conducted at 0° C. to ambient temperature in acetonitrile, THF, acetone, or other ketone solvent. Acetone or THF are the preferred solvents. Other oxidants can be employed for the transformation of 4 to 5. These reagents can include: phenyliodine diacetate (PIDA), N-bromosuccinimide (NBS), N-chlorosuccinimide (NCS), Chloramine-T, I₂O₅, but PIFA is preferred. Step 4b is initiated by the addition of TFAA. The reaction is conducted between 0° C. and ambient temperature and in the same solvents as step 4a. After reaction completion, H₂O is added to quench the reaction as well as to facilitate the crystallization of hydroxamic 6b.

The reaction scheme for step 4 may be summarized as follows:

Scheme 4:

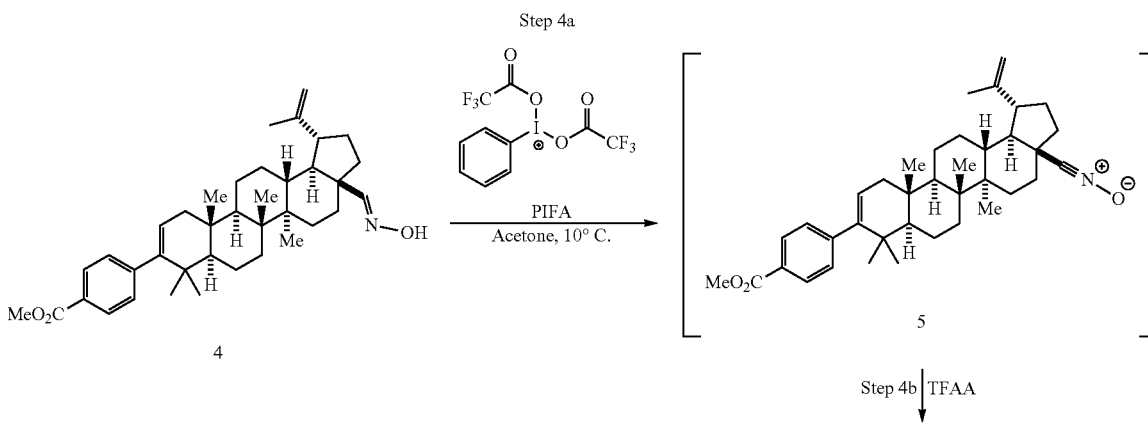

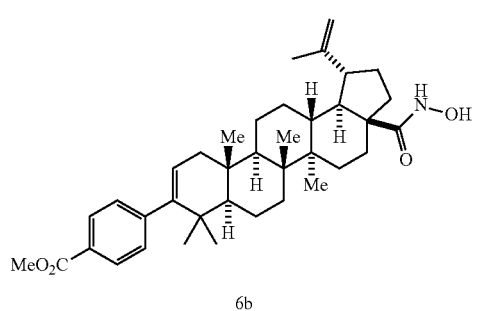

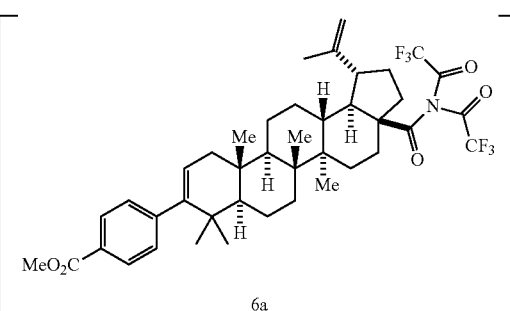

Step 5: Preparation of Compound 7

Step 5 comprises the base mediated decarboxylative rearrangement (Lossen rearrangement) of the hydroxamic acid (6b) to yield the primary amine intermediate 7. This base-mediated Lossen rearrangement (DBU, CH₃CN, 70° C.) is carried out under very mild conditions (DBU, CH₃CN, 70° C.). Applicants have surprisingly discovered that CH₃CN performs as both solvent and as an initiator for the desired rearrangement through a self-propagating mechanism.

Step 5 is catalyzed by the addition of a base. Various organic or inorganic bases can be used, but 1,8-Diazabicyclo[5.4.0]undec-7-ene (DBU) is preferred. The reaction can be conducted in various solvents and co-solvents with acetonitrile being preferred, and at elevated temperatures (typically >70° C.). Typical yields range from about 90-95% overall yield. It is believed that this sequence (steps 4+5) represents a unique and unprecedented method for the introduction of a C-17 nitrogen on the biologically important betulin framework.

The reaction scheme for step 5 may be summarized as follows:

Scheme 5:

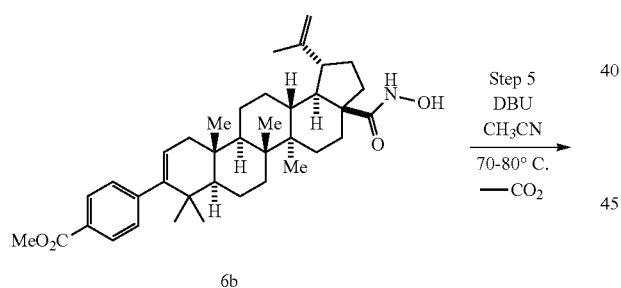

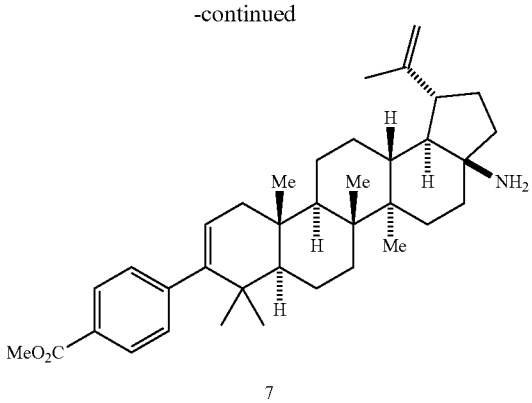

Step 6: Preparation of Compound 9

This is the penultimate step comprising the N-alkylation of 7 with 8 in presence of a base. The product 9 is then isolated as either free base or various salt forms.

Scheme 6:

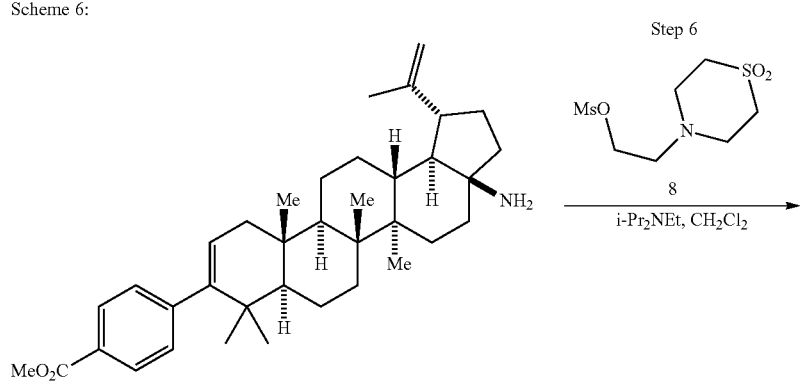

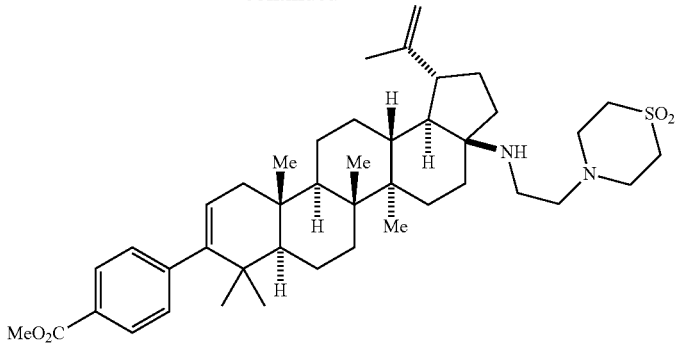

9

In a further aspect of the invention, compound 8 may be represented as:

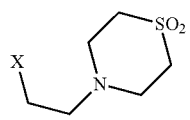

8

X = OMs, OBs, OTf, ONf, OTs, Cl, Br, or I wherein X can be any number of leaving groups, e.g., mesylate, besylate, triflate, nonaflate, tosylate, chloride, bromide and iodide, with mesylate being preferred. With respect to base identity, i-Pr$_2$NEt, triethylamine, 2,4,6 collidine, 2,6-lutidine, 2,3-lutidine, di-tertbutylpyridine, N-methylpyrrolidine, 2,6-dimethylpiperidine, 2-picoline, triallylamine, diethylaminoacetonitrile, tributylamine, N,N-dicyclohexylmethylamine, DBU, and TMSOK have been demonstrated to be suitable bases. Due to best stability and operability, the combination of mesylate 8 and i-Pr$_2$NEt in DCM is the preferred option.

Step 7: Preparation of Compound 1

This is the final step comprising the saponification of the methyl ester using aq. n-Bu$_4$NOH in IPA/H$_2$O or THF. Other bases including NaOH, KOH, and LiOH can be implemented in this process, but n-Bu$_4$NOH is preferred. The use of acetonitrile as part of a THF/H$_2$O mixture for the final crystallization is important in generating and isolating the desired mono-HCl salt/mono-hydrate form. The product from this process provides the compound of Formula I.

Scheme 7:

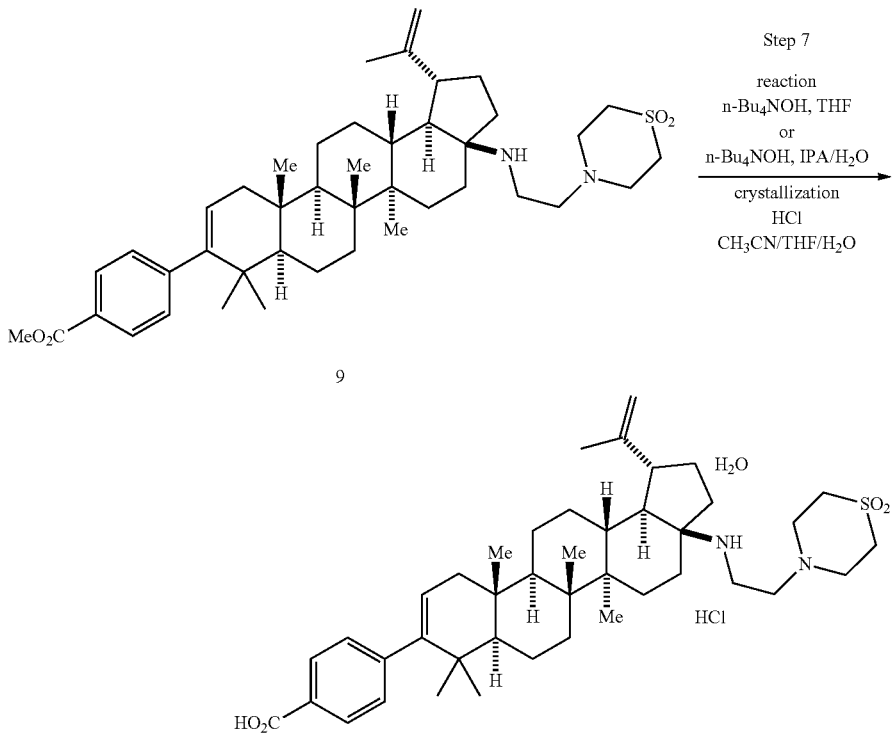

It is intended that when references are made herein to the preparations of pharmaceutical compositions containing the compound of Formula I and references are made to the treatment of patients by administering the compound of Formula I, that the references to the compound of Formula I are intended to include pharmaceutically acceptable salts and polymorphic forms of the compound of Formula I.

The active ingredient, i.e., the compound of Formula I, in such compositions typically comprises from 0.1 weight percent to 99.9 percent by weight of the composition, and often comprises from about 5 to 95 weight percent. In some cases, the pH of the formulation can be adjusted with pharmaceutically acceptable modifiers (such as calcium carbonate and magnesium oxide) to enhance the stability of the formulated compound or its delivery form. Formulations of the compound of the present disclosure can also contain additives for enhancement of absorption and bioavailability.

The compound of Formula I can be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants can also be included.

Other suitable carriers for the above noted compositions can be found in standard pharmaceutical texts, e.g. in "Remington's Pharmaceutical Sciences", 19th ed., Mack Publishing Company, Easton, Pa., 1995. Further details concerning the design and preparation of suitable delivery forms of the pharmaceutical compositions of the disclosure are known to those skilled in the art.

When the compound is formulated together with a pharmaceutically acceptable carrier, the resulting composition can be administered in vive to mammals, such as man, to inhibit or to treat or prevent HIV virus infection.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of the compound of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention can be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents can be utilized in the pharmaceutical compositions, and are those utilized in the art of pharmaceutical preparations.

When administered orally as a suspension, these compositions are prepared according to techniques typically known in the art of pharmaceutical formulation and can contain microcrystalline cellulose for imparting bulk, alginic acid or sodium alginate as a suspending agent, methylcellulose as a viscosity enhancer, and sweeteners/flavoring agents known in the art. As immediate release tablets, these compositions can contain microcrystalline cellulose, dicalcium phosphate, starch, magnesium stearate and lactose and/or other excipients, binders, extenders, disintegrants, diluents, and lubricants known in the art.

When orally administered, the pharmaceutical compositions of the invention can be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, can also be added. For oral administration in a capsule form, useful carriers/diluents include lactose, high and low molecular weight polyethylene glycol, and dried corn starch. When aqueous suspensions are administered orally, the active ingredient is combined with emulsifying and suspending agents. If desired, certain sweetening and/or flavoring and/or coloring agents can be added.

The compound of Formula I can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The pharmaceutical compositions can be in the form of a sterile injectable preparation, for example, as a sterile injectable aqueous or oleaginous suspension. This suspension can be formulated according to techniques known in the art using suitable dispersing or wetting agents and suspending agents. The details concerning the preparation of such compounds are known to those skilled in the art.

The injectable solutions or suspensions can be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Also contemplated herein is the compound of Formula I in combination with one or more other agents useful in the treatment of AIDS. For example, the compounds of this disclosure can be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, AIDS related complex (ARC) (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |

-continued

| Drug Name | Manufacturer | Indication |
|---|---|---|
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingelheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

-continued

| Drug Name | Manufacturer | Indication |
|---|---|---|
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |

| Drug Name | Manufacturer | Indication |
|---|---|---|
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | Pneumocystic Pneumonia PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |

-continued

| Drug Name | Manufacturer | Indication |
| --- | --- | --- |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compound of Formula I can be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*, Meanwell, Nicholas A.; Kadow, John F. Current Opinion in Drug Discovery & Development (2003), 6(4), 451-461. Specifically, the compounds can be utilized in combination with attachment inhibitors, fusion inhibitors, and chemokine receptor antagonists aimed at either the CCR5 or CXCR4 co-receptor. HIV attachment inhibitors are also set forth in U.S. Pat. No. 7,354,924 and US 2005/0209246. It will be understood that the scope of combinations of the compound of Formula I with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of Formula I and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This can be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine. In such combinations the compound of Formula I and other active agents can be administered separately or in conjunction. In addition, the administration of one element can be prior to, concurrent to, or subsequent to the administration of other agent(s).

In another aspect, these methods are useful for inhibiting viral replication in a patient. Such methods can be useful in treating or preventing HIV disease.

The compounds of Formula I can also be used as laboratory reagents. The polymorphs can be instrumental in providing research tools for designing of viral replication assays, validation of animal assay systems and structural biology studies to further enhance knowledge of the HIV disease mechanisms.

The compounds of Formula I can also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The invention can be embodied in other specific forms without departing from the spirit or essential characteristics thereof. The foregoing aspects are to be considered in all respects illustrative rather than limiting on the invention described herein. In the various aspects of the present invention, where the term "comprising" or "comprises" is used, it is also contemplated that in certain aspects the term "consisting essentially of" or "consists essentially of" can be used, and it is also contemplated that in other certain aspects the term "consisting of" or "consists of" can be used.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight. Also, throughout the disclosure the term "weight" is used. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

The foregoing description is merely illustrative and should not be understood to limit the scope or underlying principles of the invention in any way. Indeed, various modifications of the invention, in addition to those shown and described herein, will become apparent to those skilled in the art from the foregoing description and examples. Such modifications are also intended to fall within the scope of the appended claims.

What is claimed is:

1. A method for making a compound of Formula I:

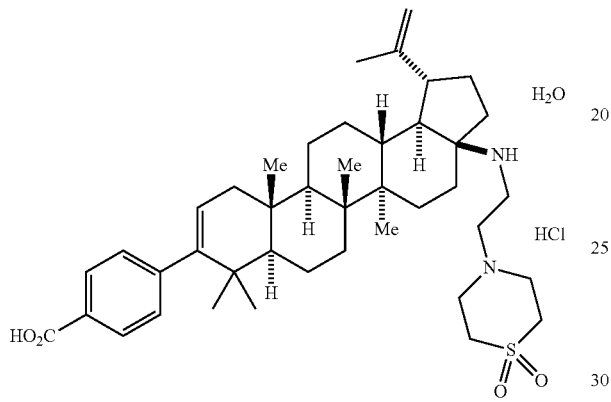

which comprises:

(a) oxidizing betulin to form a compound of Formula 1

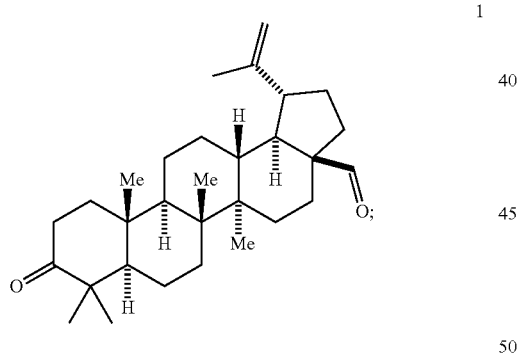

(b) contacting compound 1 with a compound of Formula 2a

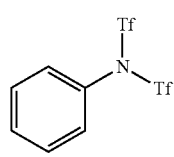

in the presence of a reagent to form a compound of Formula 2b

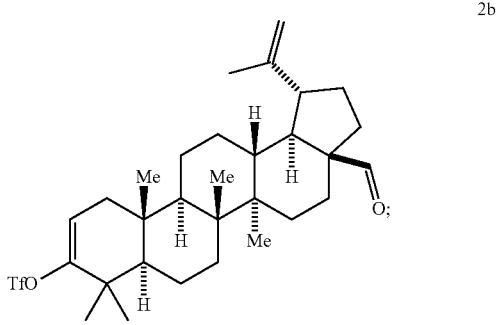

(c) contacting compound 2b with a compound of Formula 3a

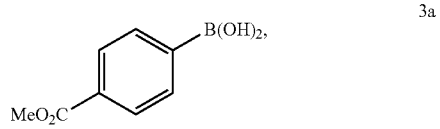 [SMILES: COC(=O)c1ccc(B(O)O)cc1]

in the presence of PdCl$_2$Xantphos and aqueous K$_3$PO$_4$ to form a compound of Formula 3b

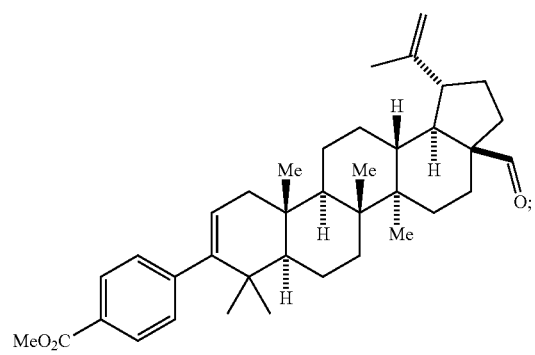

(d) contacting compound 3b with hydroxylamine to form a compound of Formula 4

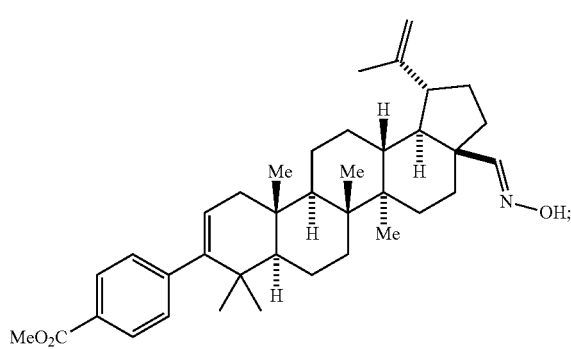

(e) contacting compound 4 with an oxidant to form a compound of Formula 5

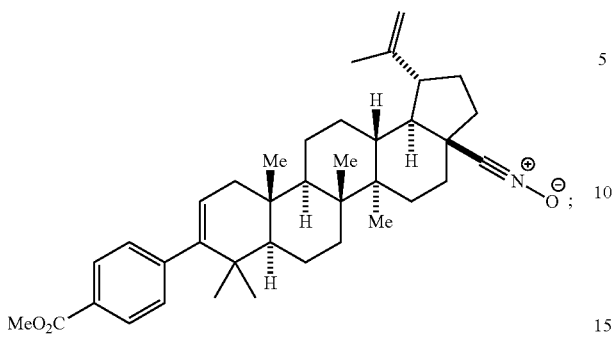

5

(f) contacting compound 5 with TFAA and water to form a compound of Formula 6b

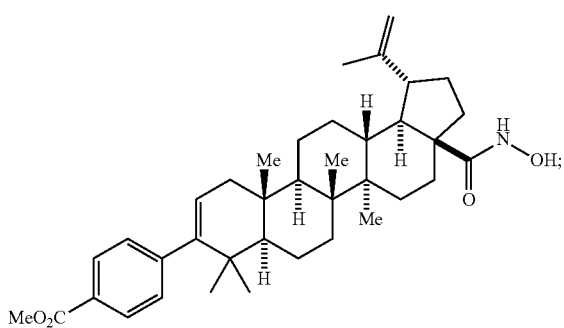

6b (g) contacting compound 6b with a base and heat to form a compound of Formula 7

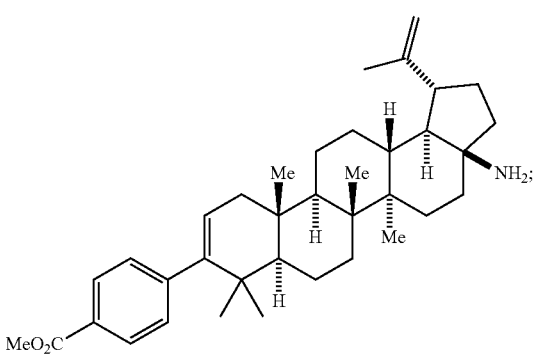

7

(h) contacting compound 7 with a compound of Formula 8

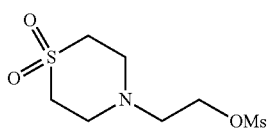

8 and i-Pr$_2$NEt and CH$_2$Cl$_2$ to form a compound of Formula 9

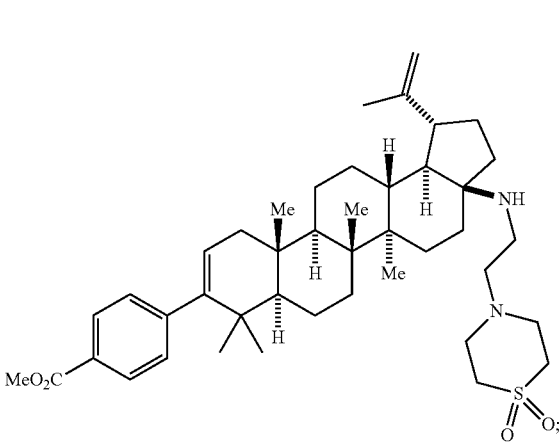

9 and (i) contacting compound 9 with an aqueous base to form the compound of Formula I.

2. The process as claimed in claim 1 wherein in step (a), said oxidation is performed in the presence of a solvent comprising a carbodiimide and dimethylsulfoxide in dichloromethane.

3. The process as claimed in claim 2 wherein said carbodiimide is selected from 1-ethyl-3-(3-dimethylaminopropyl)carbodiimide, diisopropylcarbodiimide and dicyclohexylcarbodiimide.

4. The process as claimed in claim 3 wherein said carbodiimide is ethyl-3-(3-dimethylaminopropyl)carbodiimide.

5. The process as claimed in claim 4 further utilizing a catalytic acid in step (a).

6. The process as claimed in claim 5 wherein said catalytic acid is selected from para-toluene sulfonic acid, pyridinium p-toluenesulfonate, dichloroacetic acid, and H$_3$PO$_4$.

7. The process as claimed in claim 6 wherein said catalytic acid is pyridinium p-toluenesulfonate.

8. The process as claimed in claim 1 wherein in step (b) said reagent is selected from lithium diisopropyl amide and M-HMDS, wherein M is selected from Na, K, or Li and HMDS is hexamethyldisilazane.

9. The process as claimed in claim 8 wherein said reagent is sodium hexamethyldisilazide.

10. The process as claimed in claim 1 wherein step (c) is conducted in the presence of a solvent.

11. The process as claimed in claim 10 wherein the solvent is tetrahydrofuran.

12. The process as claimed in claim 1 wherein in step (e) said oxidant is phenyliodine (bis)trifluoroacetate.

13. The process as claimed in claim 1 wherein in step (g) said base is 1,8-diazabicyclo[5.4.0]undec-7-ene.

14. The process as claimed in claim 1 wherein in step (i) said base is n-Bu$_4$NOH in isopropyl alcohol or tetrahydrofuran.

15. A method for making a compound of Formula I:

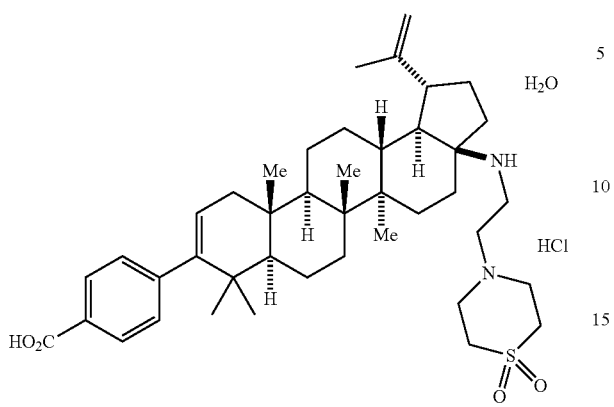

which comprises:
(a) oxidizing betulin to form a compound of Formula 1

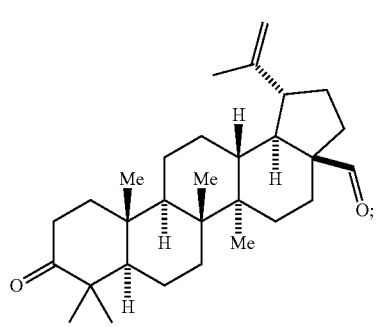

(b) contacting compound 1 with a compound of Formula 2a

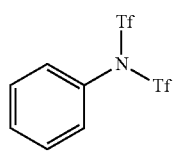

in the presence of a reagent to form a compound of Formula 2b

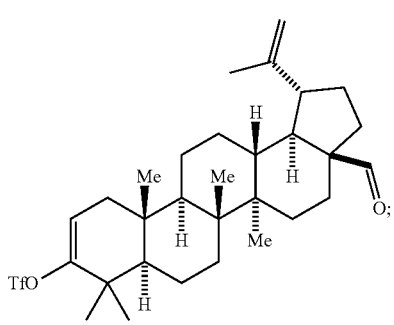

(c) contacting compound 2b with a compound of Formula 3a'

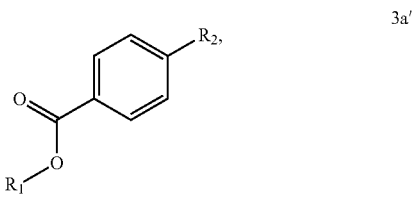

wherein $R^1$ is selected from alkyl, aryl, and substituted aryl, and $R_2$ is selected from a boronic acid, pinacol-boronate ester, or isopropyl boronate ester, said contacting being conducted in the presence of $PdCl_2$xantphos and aqueous $K_3PO_4$ to form a compound of Formula 3b'

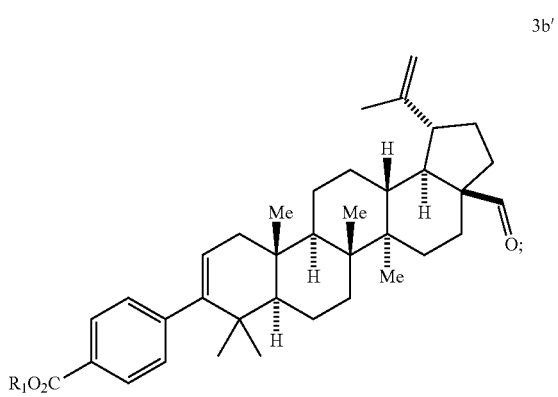

(d) contacting compound 3b' with hydroxylamine to form a compound of Formula 4'

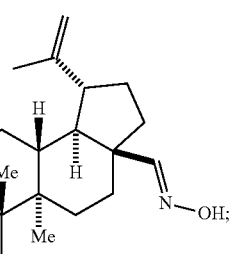

(e) contacting compound 4' with an oxidant to form a compound of Formula 5'

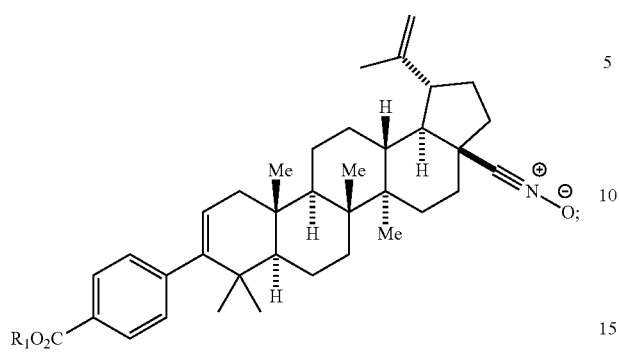

(f) contacting compound 5' with TFAA and water to form a compound of Formula 6b'

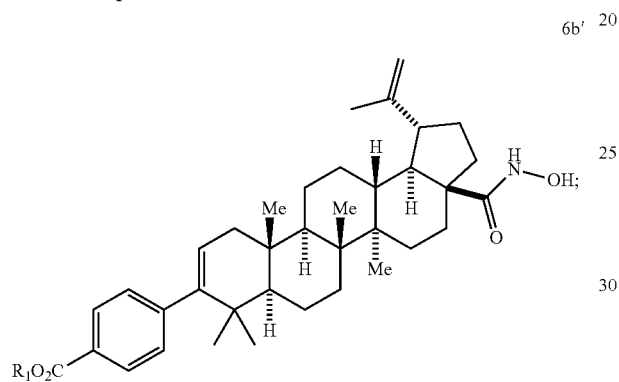

(g) contacting compound 6b' with a base and heat to form a compound of Formula 7'

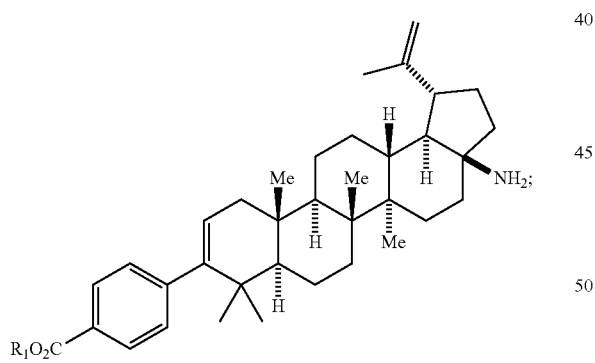

(h) contacting compound 7' with a compound of Formula 8'

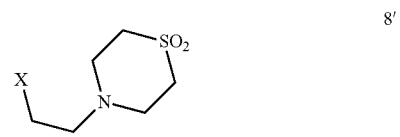

wherein X is selected from mesylate, besylate, triflate, nonaflate, tosylate, chloride, bromide and iodide, to form a compound of Formula 9'

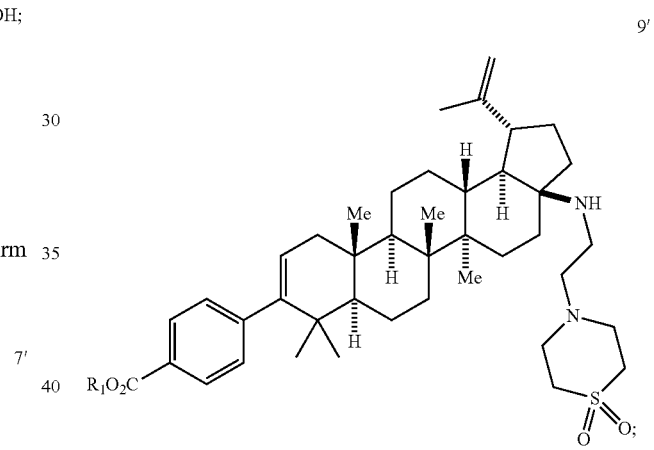

and (i) contacting compound 9' with an aqueous base to form the compound of Formula I.

* * * * *